US010048207B2

(12) United States Patent
Kang et al.

(10) Patent No.: US 10,048,207 B2
(45) Date of Patent: *Aug. 14, 2018

(54) COMPOSITIONS AND KITS COMPRISING A MEMBRANE PERMEABLE MARKER THAT IS CONVERTED INTO A DETECTABLE MARKER INSIDE A MICROVESICLE, AND METHODS FOR DETECTING AND ANALYZING MICROVESICLE

(71) Applicant: Samsung Electronics Co., Ltd., Suwon-si, Gyeonggi-do (KR)

(72) Inventors: Hyun-ju Kang, Hwaseong-si (KR); Ye-ryoung Yong, Seoul (KR); Myo-yong Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 939 days.

This patent is subject to a terminal disclaimer.

(21) Appl. No.: 13/857,089

(22) Filed: Apr. 4, 2013

(65) Prior Publication Data

US 2014/0080136 A1    Mar. 20, 2014

(30) Foreign Application Priority Data

Sep. 18, 2012    (KR) .................... 10-2012-0103503

(51) Int. Cl.
*G01N 21/64*  (2006.01)
*G01N 33/58*  (2006.01)

(52) U.S. Cl.
CPC ....... *G01N 21/6486* (2013.01); *G01N 33/582* (2013.01)

(58) Field of Classification Search
CPC ..................... G01N 33/582; G01N 21/64
See application file for complete search history.

(56) References Cited

U.S. PATENT DOCUMENTS

| 5,179,120 | A | * | 1/1993 | Vogel | A61K 41/0057 |
| | | | | | 514/410 |
| 5,616,719 | A | * | 4/1997 | Davalian | C07D 311/20 |
| | | | | | 546/334 |
| 5,869,689 | A | * | 2/1999 | Zhang | C07F 5/022 |
| | | | | | 372/39 |
| 6,107,066 | A | * | 8/2000 | Tsien | C07D 209/08 |
| | | | | | 435/173.4 |
| 6,511,815 | B1 | | 1/2003 | Burke et al. | |
| 6,743,638 | B1 | | 6/2004 | Tsilosani et al. | |
| 7,553,632 | B2 | | 6/2009 | Niles et al. | |

(Continued)

FOREIGN PATENT DOCUMENTS

KR    2013-0032646 A    4/2013

OTHER PUBLICATIONS

Van der Pol et al., "Classification, functions, and clinical relevance of extracellular vesicles", Pharmacol Rev. (Jul. 2012) 64(3):676-705. Epub Jun. 21, 2012.*

(Continued)

*Primary Examiner* — Scott Long
*Assistant Examiner* — Gary E Hollinden
(74) *Attorney, Agent, or Firm* — Leydig, Voit & Mayer, Ltd.

(57) ABSTRACT

Provided are compositions, kits, and methods for detecting a vesicle comprising a membrane permeable marker that is converted into a detectable marker inside the vesicle.

10 Claims, 5 Drawing Sheets

(56) References Cited

U.S. PATENT DOCUMENTS

| | | | |
|---|---|---|---|
| 7,951,550 B2 | 5/2011 | Cali et al. | |
| 2003/0009023 A1* | 1/2003 | Luyten | A61K 38/1709 536/23.5 |
| 2003/0022277 A1* | 1/2003 | Soppet | C07K 14/70571 435/69.1 |
| 2004/0156787 A1* | 8/2004 | Roncucci | A61K 41/0057 424/9.61 |
| 2006/0275835 A1* | 12/2006 | Jacobson | G01N 33/5008 435/7.2 |
| 2009/0029870 A1* | 1/2009 | Ward | G01N 15/1404 506/9 |
| 2009/0220944 A1* | 9/2009 | Fais | G01N 33/567 435/5 |
| 2009/0253145 A1 | 10/2009 | Kilpatrick et al. | |
| 2009/0258379 A1 | 10/2009 | Klein et al. | |
| 2010/0029791 A1 | 2/2010 | Ichikawa et al. | |
| 2010/0081159 A1 | 4/2010 | Lebedeva et al. | |
| 2010/0113290 A1* | 5/2010 | Klass | C12Q 1/6809 506/7 |
| 2010/0330584 A1* | 12/2010 | Gee | A61K 31/353 435/7.1 |
| 2011/0124033 A1* | 5/2011 | Licher | G01N 33/6872 435/29 |
| 2011/0189266 A1* | 8/2011 | Fayad | A61K 9/0019 424/450 |
| 2013/0078658 A1 | 3/2013 | Park et al. | |
| 2013/0157300 A1 | 6/2013 | Park et al. | |
| 2013/0178383 A1* | 7/2013 | Spetzler | G01N 33/5432 506/9 |

OTHER PUBLICATIONS

European Examination Report for EP Application No. 13170397.7 dated Jul. 23, 2015.

Sohn, Yang-Sung et al., "Redidstribution of accumulated cell iron: a modality of chelation with therapeutic implications", *Blood*, vol. 111, No. 3, (2008).

Mazzucato, Mario et al, "Distrinct spatio-temporal $Ca^{2+}$ signaling elicited by integrin a2B1 nad glycoprotein Vl under flow", *Blood*, vol. 114, No. 13, (2009).

Bernimoulin et al., "Differential stimulation of monocytic cells results in distinct populations of microparticles," *J. of Thrombosis and Haemostasis*, 7(6):1019-1028 (2009).

Stahl et al., "Complement activation on platelet-leukocyte complexes and microparticles in enterohemorrhagic *Escherichia coil*—induced hemolytic uremic syndrome," *Blood*, 117(20): 5503-5513 (2011).

Wang et al., "Monocytic microparticles activate endothelial cells in an IL-1β-dependent manner," *Blood*, 118(8): 2366-2374 (2011).

European Patent Office, Extended European Search Report in European Patent Application No. 13170397.7, dated Jul. 30, 2013.

Laulagnier, et al, "Characterization of exosome subpopulations from RBL-2H3 cells using fluorescent lipids", *Blood Cells, Molecules & Diseases*, 35:116-121 (2005).

Parolini, et al, "Microenvironmental pH Is a Key Factor for Exosome Traffic in Tumor Cells",*The Journal of Biological Chemistry*, 284 (49): 34211-34222 (2009).

Tian, et al, "Visualizing of the cellular uptake and intracellular trafficking of exosomes by live-cell microscopy", *The Journal of Cellular Biochemistry*, 111:488-496 (2010).

Korean Office Action in Application No. 10-2012-0103503 dated Mar. 16, 2018.

Mitchell et al., "Can urinary exosomes act as treatment response markers in prostate cancer?" *Journal of Translational Medicine*, 7:4, pp. 1-13 (2009).

Di Virgilio et al., "Inhibition of Fura-2 sequestration and secretion with organic anion transport blockers", *PubMed, Cell Calcium*, 11(2-3) (1990).

\* cited by examiner

COMPOSITIONS AND KITS COMPRISING A MEMBRANE PERMEABLE MARKER THAT IS CONVERTED INTO A DETECTABLE MARKER INSIDE A MICROVESICLE, AND METHODS FOR DETECTING AND ANALYZING MICROVESICLE

CROSS-REFERENCE TO RELATED APPLICATIONS

This application claims the benefit of Korean Patent Application No. 10-2012-0103503, filed on Sep. 18, 2012 in the Korean Intellectual Property Office, the disclosure of which is incorporated herein by reference.

BACKGROUND

1. Field

The present disclosure relates to compositions, kits, and methods for detecting and analyzing vesicles.

2. Description of the Related Art

Microvesicles are small membrane-bound vesicles that exist in or are secreted from various types of cells. Microvesicles include (i) exosomes, membraneous vesicles 30 to 100 nm in diameter that are secreted by a wide range of mammalian cell types, (ii) ectosomes (shedding microvesicles (SMVs)), large membranous vesicles 50 to 1000 nm in diameter that are released directly from plasma membranes, and (iii) apoptotic blebs: vesicles 50 to 5000 nm in diameter that are secreted from dying cells.

Using an electron microscope, it has been observed that exosomes are not directly released from plasma membranes, but rather originate from specific intracellular regions called multivesicular bodies (MVBs), which fuse with the plasma membrane and are then released into the extracellular environment as exosomes. Exosomes are secreted from various different cell types under both normal and pathologic states. Erythrocytes, various types of immunologic cells (including B-lymphocytes, T-lymphocytes, dendritic cells, platelets, and macrophages), and tumor cells produce and secrete exosomes. Microvesicles may contain microRNAs (miRNAs), which may be used to diagnose various conditions, including cancer.

Existing methods of detecting and characterizing microvesicles are performed by immuno-capturing microvesicles and then detecting a protein in the microvesicles using a labeled antibody. However, such methods may cause a bias due to masking of antibody recognition sites by changes in a protein structure, microvesicle heterogeneity, protein interactions, etc. In addition, detection results may be inaccurate due to contamination by external proteins, for example, secreted or fragmented proteins. Furthermore, many existing methods require a complicated process, a high-cost apparatus, or a large sample volume.

Therefore, there is a need for improved methods of detecting and quantifying microvesicles, analyzing microvesicle proteins, glycoproteins, or lipids, and screening ligands that have binding affinity for microvesicles.

SUMMARY

Provided are compositions for detecting vesicles.
Provided are kits for detecting vesicles.
Provided are methods for analyzing vesicles within samples.

Additional aspects will be set forth in part in the description which follows and, in part, will be apparent from the description, or may be learned by practice of the presented embodiments.

Provided is a composition for detecting a vesicle comprising a membrane permeable marker that is converted into a detectable marker inside the vesicle.

"Vesicle" refers to a membranous structure bound by a lipid bilayer. For example, the vesicle may be a liposome or a microvesicle. A microvesicle is a small membrane-bound structure that originates from cells. The term "microvesicle" may be used interchangeably with the terms "circulating microvesicle" or "microparticle." Microvesicles may exist inside cells or may be secreted from cells. Secreted microvesicles may include exosomes, ectosomes (shedding microvesicles (SMVs)), apoptotic blebs, or any combination thereof. Exosomes may be membranous vesicles of about 30 to about 100 nm diameter that originate from phagocytes. Ectosomes (SMVs) may be large membranous vesicles of about 50 to about 1000 nm in diameter that are directly released from plasma membranes. Apoptotic blebs may be vesicles of about 50 to about 5000 nm in diameter that are secreted from dying cells. Microvesicles may contain microRNAs (miRNAs) or messenger RNAs (mRNAs). Surface proteins of microvesicles may serve as disease-specific markers.

The membrane permeable marker may be converted into a fluorescent material within the vesicle. "Fluorescent material" refers to a material that emits light under a change of physical conditions or chemical treatments. The membrane permeable marker may be a non-fluorescent material outside a vesicle, but may be converted into a fluorescent material inside the vesicle. The conversion may be performed by enzymes (e.g., esterase) within the vesicle. The membrane permeable marker may be a hydrophobic material outside the vesicle, but may be converted into a hydrophilic material inside the vesicle. A hydrophobic material will be able to permeate a vesicle membrane, but a hydrophilic material will not be able to permeate a vesicle membrane.

The marker may be, for example, calcein-AM (calcein-acetoxymethyl ester), fura-2-AM (Fura-2-acetoxymethyl ester), indo-1-AM (indo-1-acetoxymethyl ester), indo-5F-AM (indo-5F-acetoxymethyl ester), quin-2-AM (quin-2-acetoxymethyl ester), 5-CFDA-AM (5-carboxyfluorescein diacetate-acetoxymethyl ester), BAPTA-AM (bis(2-aminophenoxy)ethane tetraacetic acid-acetoxymethyl ester), 5,5'-difluoro BAPTA-AM, 5,5'-dimethyl BAPTA-AM, 5,5'-dinitro BAPTA-AM, BCECF-AM (2',7'-bis-(2-carboxyethyl)-5-(and-6)-carboxyfluorescein acetoxymethyl ester), dihydrocalcein-AM (dihydrocalcein-acetoxymethyl ester), EGTA-AM (EGTA-acetoxymethyl ester), fluo-3-AM (Fluo-3-acetoxymethyl ester), fluo-8-AM (Fluo-8-acetoxymethyl ester), rhod-2-AM (rhod-2-acetoxymethyl ester), rhod-4-AM (rhod-2-acetoxymethyl ester), rhod-5F-AM (rhod-5F-acetoxymethyl ester), rhod-5N-AM (rhod-5N-acetoxymethyl ester), X-rhod-1-AM (X-rhod-1-acetoxymethyl ester), or any combination thereof.

The composition may further include an organic anion transport inhibitor. "Organic anion transport inhibitor" refers to a material that inhibits the organic anion transport system. For example, the organic anion transport inhibitor may be sulfinpyrazone, probenecid, betamipron, cilastatin, 8-(noradamantan-3-yl)-1,3-dipropylxanthine, or any combination thereof. The efficiency vesicle detection may be enhanced by using the organic anion transport inhibitor.

Provided is a kit for detecting a vesicle comprising a membrane permeable marker that is converted into a detectable marker inside the vesicle. The kit may further comprise an organic anion transport inhibitor.

Provided is a method of analyzing a vesicle in a sample comprising contacting a sample with a membrane permeable marker that is converted into a detectable marker inside the vesicle; and measuring a signal of the detectable marker.

The sample may be a body fluid sample or cell culture sample. The body fluid may be, for example, urine, mucus, saliva, tears, blood plasma, blood serum, sputum, spinal fluid, hydrothorax, nipple aspirate, lymph, tracheolar fluid, intestinal fluid, genitourinary tract fluid, breast milk, lymph system fluid, semen, cerebrospinal fluid, tracheal system fluid, ascites, cystic tumor fluid, amniotic fluid, or any combination thereof.

The contacting may be performed in vitro. For example, the contacting may be performed at room temperature. For example, the contacting may be performed while mixing reactants.

Various methods according to kinds of a fluorescent material may be used for measuring the signal. For example, if the fluorescent material is a fluorescent protein, the fluorescent intensity generated by the fluorescent protein when illuminated by ultraviolet light may be measured by using a fluorophotometer.

The method of analyzing a vesicle may include, for example, a method of detecting a vesicle, a method of analyzing vesicle proteins, glycoproteins, lipids, or nucleic acids, or any combination thereof.

The method may further comprise incubating the sample with an organic anion transport inhibitor, as previously described, before measuring the signal of the detectable marker. The incubating may be performed in vitro. For example, the incubating may be performed at room temperature. For example, the incubating may be performed while mixing reactants. The incubating of the sample with the organic anion transport inhibitor may be performed before, after or at the same time as the contacting of the sample with the membrane permeable marker that is converted into the detectable marker inside the vesicle. The vesicle detecting efficiency may be enhanced by incubating the sample with the organic anion transport inhibitor.

The method may further include incubating a ligand with the vesicle to analyze a vesicle protein, glycoprotein or lipid (e.g., a phospholipid or cholesterol) before measuring the signal of the detectable marker. The ligand may, for example, have binding affinity for a vesicle protein, glycoprotein, or lipid. The ligand may be, for example, a material having binding affinity for a protein, a substrate of an enzyme, a coenzyme, a regulatory factor, a material that specifically binds to a receptor, a lectin, an antigen, an antibody, a hormone, a neurotransmitter, a phospholipid-binding protein, a protein that includes pleckstrin homology (PH) domain, or a cholesterol-binding protein. The incubating may be performed in vitro. For example, the incubating may be performed at room temperature. For example, the incubating may be performed while mixing reactants. Vesicle proteins, glycoproteins and lipids may be analyzed by measuring the signal the detectable marker. The ligand may be fixed on a solid support. The solid support may be, for example, a polystyrene plate or a bead. The incubating of the ligand with the vesicle may be performed before, after or at the same time as the contacting of the sample with the membrane permeable marker that is converted into the detectable marker inside the vesicle. If the ligand is fixed on a solid support, the method may further comprise washing a vesicle that is bound to the ligand fixed on the solid support.

The method may further comprise incubating at least two kinds of ligands with the vesicle to screen for ligands having binding affinity to the vesicle. The ligand may, for example, have binding affinity for a vesicle protein, glycoprotein, or lipid. The ligand may be, for example, a material having binding affinity for a protein, a substrate of an enzyme, a coenzyme, a regulatory factor, a material that specifically binds with receptors, a lectin, an antigen, an antibody, a hormone, a neurotransmitter, a phospholipid-binding protein, a protein that includes pleckstrin homology (PH) domain, or a cholesterol-binding protein.

The use of the compositions, kits, and methods described herein reduces or eliminates detection bias due to types of detection targets or external protein contamination, and allows for detection of vesicles in a short amount of time using a simple process, even from low-quantity samples. Furthermore, vesicle proteins, glycoproteins, lipids, or nucleic acids may be analyzed, and ligands with binding affinity for vesicles may be screened. Detection of vesicles having disease-specific markers may be used to diagnose or monitor a disease.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

Example 1. Detection and Quantification of Microvesicles

0 µl, 0.2 µl, 0.5 µl, 1 µl, 2 µl, 5 µl, 10 µl, and 20 µl of plasma were incubated in wells of plates (Pierce) coated with anti-CD9 antibodies (R&D systems) and then were washed, and microvesicles with CD9 proteins were separated from the plasma. Afterwards, the microvesicles separated from the plasma were stained by adding calcein AM (Sigma) to each well and performing incubation. After washing the reactant, a fluorophotometer (Beckman, DTX800) was used to measure fluorescence intensity. As control group, 0 µl, 0.2 µl, 0.5 µl, 1 µl, 2 µl, 5 µl, 10 µl, and 20 µl of plasma were incubated in a plate without an antibody, and then were washed. Afterwards, the plate was stained by adding calcein AM (Sigma), the reactant was washed, and then fluorescence intensity was measured. A result of detecting microvesicles in plasma is shown in FIG. 2A (○: control group, ●: experimental group, X axis: an amount of plasma (µl), Y axis: fluorescence intensity, R: correlation coefficient).

As a comparative example, magnetic beads (Invitrogen) were coated with the anti-CD9 antibodies (R&D systems) as mentioned above, and incubated with about 0 µl to about 300 µl of plasma. After incubation, the beads were washed, and microvesicles with CD9 proteins were separated from the plasma. Afterwards, LDX sample buffer and reductant (Invitrogen) were incubated with the separated microvesicles to denature and reduce proteins of the microvesicles. The lysed microvesicles were subject to electrophoresis to separate proteins, and western blotting was performed using anti-CD9 antibody (Novus Biologicals). The result is shown in FIG. 2B.

Figure 1:
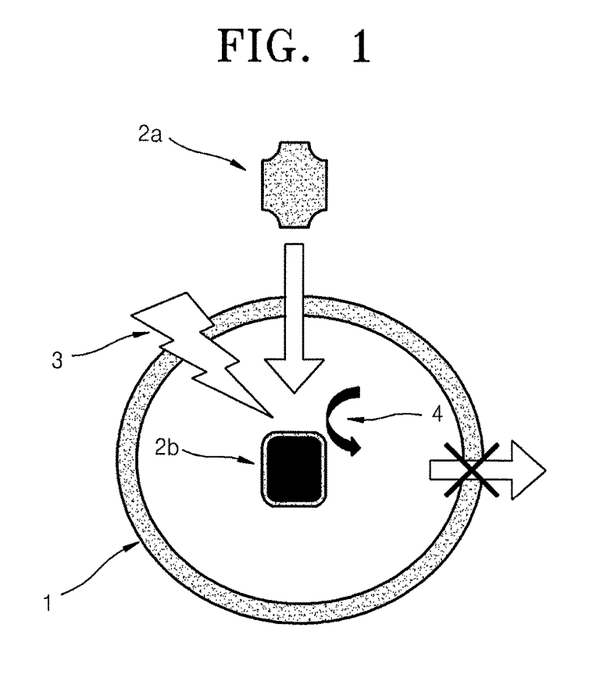
FIG. 1 is a diagram that illustrates a method of analyzing vesicles using a membrane permeable marker that is converted into a detectable marker inside a vesicle. "1" represents a vesicle bound by a lipid layer, "2a" represents a membrane permeable marker, "2b" represents a membrane permeable marker converted into a detectable marker, "3" represents a signal originating from the detectable marker, and "4" represents a reaction that converts the membrane permeable marker into the detectable marker.
Figure 2A:
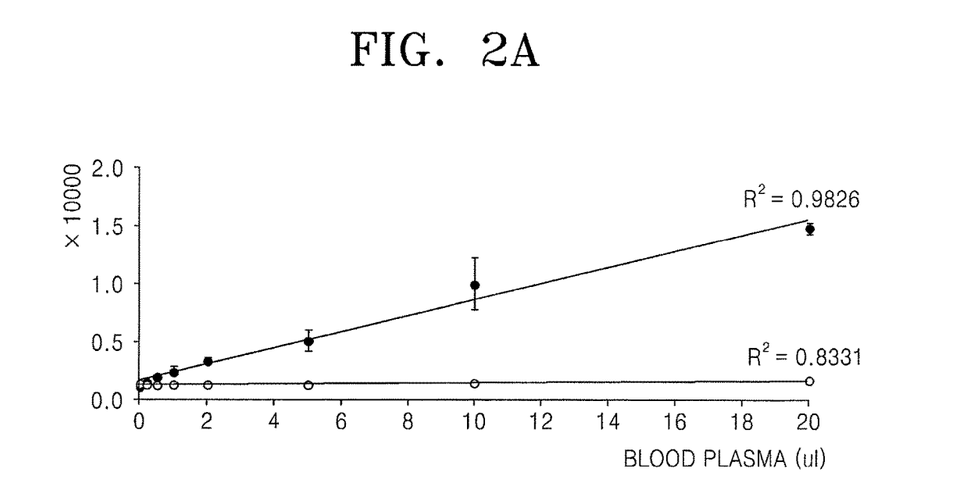
FIGS. 2A and 2B are a graph and a gel image, respectively, showing the results of detecting and quantifying microvesicles in blood plasma (○: control group, ●: experimental group, X axis: an amount of plasma (µl), Y axis: fluorescence intensity, R: correlation coefficient).
Figure 2B:
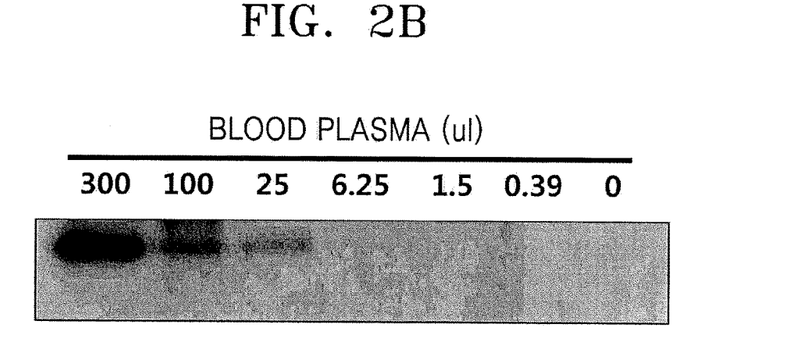

As shown in FIG. 2B, the detection limit to detect microvesicles in plasma was 25 µl for the western blotting method, but as shown in FIG. 2A, was 2 µl for the calcein-AM method. Therefore, the detection sensitivity of the calcein-AM method is about 12.5 times higher than the western blotting method.

Example 2. The Effects of Target Proteins on the Detection and Quantification of Microvesicles The comparative example of Example 1 detects microvesicles indirectly by detecting microvesicle surface proteins (target proteins) using Western blotting. Example 2 shows the effects of target proteins on the detection and quantification of microvesicles using the Western blotting method.

Figure 3A:
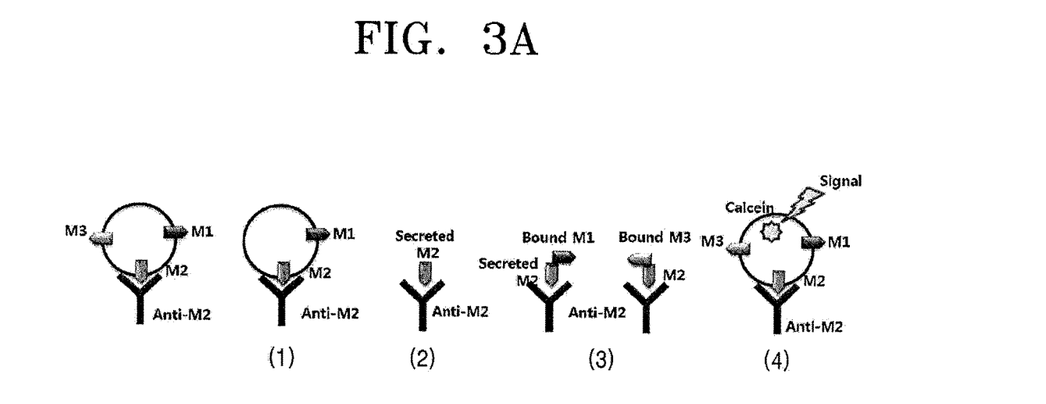
FIGS. 3A and 3B are a diagram and a gel image, respectively, that illustrate the effects of detection targets on detection of and quantification of microvesicles.
Figure 3B:
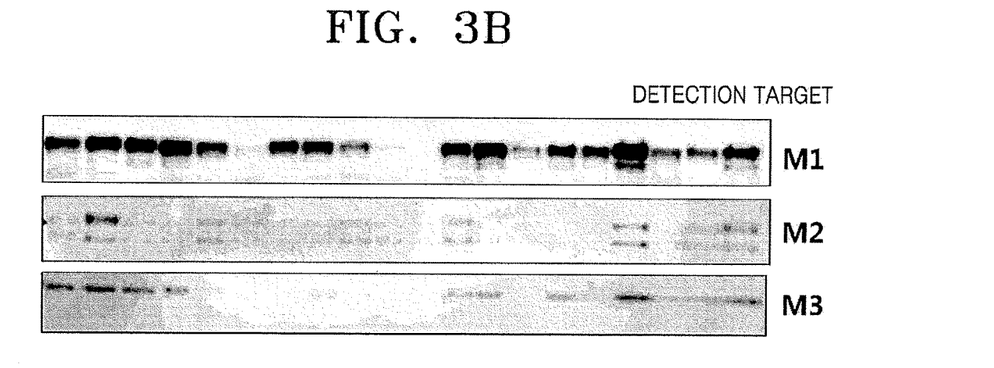

After coating an anti-M2 antibody, which binds microvesicle surface protein (M2), on magnetic beads (Invitrogen), the beads were incubated with 300 µl of plasma to separate microvesicles from the blood plasma. Anti-M2 antibody, in addition to antibodies that target other microvesicle surface proteins (M1, M3), were then used to detect microvesicles via the western blotting method of Example 1. The result is shown in FIG. 3B.

The result of the western blotting method is affected by microvesicle heterogeneity, e.g., not all microvesicles may contain the target protein, and secreted or fragmented proteins. In FIG. 3A, M1, M2, and M3 are different kinds of surface proteins of a vesicle, wherein M2 is a target for an anti-M2 antibody. The star symbol represents calcein activated inside a vesicle, and the lightning symbol represents a fluorescence signal released from the activated calcein. Although M1, M2, and M3 are microvesicle surface markers, the amount of microvesicle separated is different according to the chosen detection target used in methods such as Western blotting after immuno-precipitation. Detection biases arise when (1) captured microvesicles are micovesicles having only M1 and M2, but not M3, (2) secreted or fragmented target proteins are captured, or (3) secreted or fragmented target proteins are bound to other proteins to form a complex (M2+M1, M2+M3, or M1+M2+M3). The (4) calcein-AM detection method of the Example 1 minimized these detection biases, since microvesicles are detected directly, not indirectly via target proteins.

Example 3. Identification of the Effect of Protein Contamination on the Detection and Quantification of Microvesicles Example 3 shows the effect of protein contamination on the detection and quantification of microvesicles. In particular, Example 3 shows that the calcein-AM detection method of Example 1 minimized detection biases due to contaminating proteins, such as secreted or fragmented proteins. Microvesicles were not added to the reaction mixture in Example 3. HER2, a microvesicle surface protein, was used as the contaminating protein.

Figure 4A:
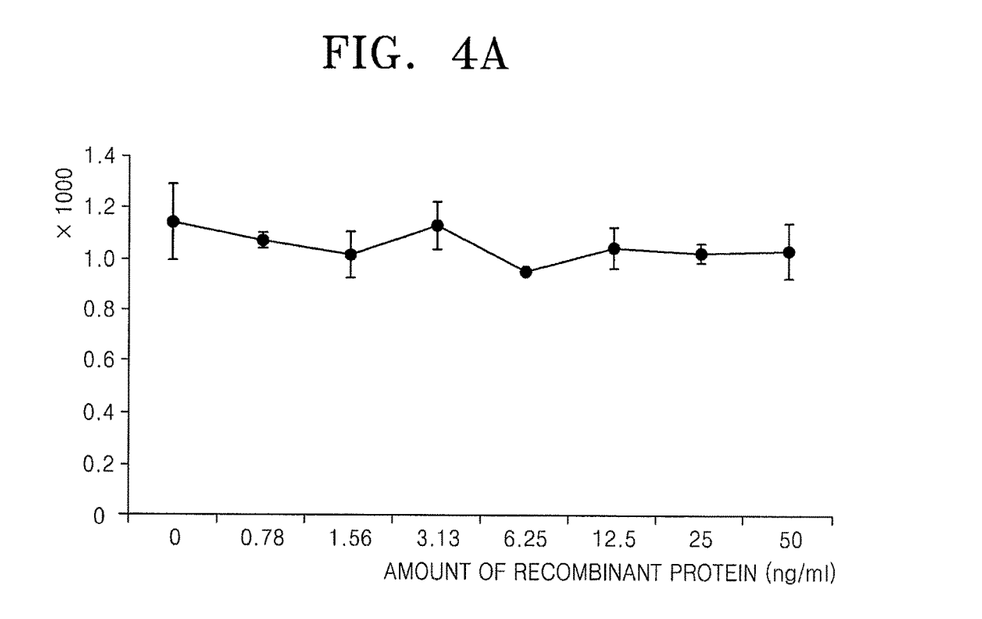
FIGS. 4A and 4B are graphs that illustrate the effect of external protein contamination on detection and quantification of microvesicles (X axis: amount of protein (ng/ml), Y axis: fluorescence intensity).

About 0.78 ng/ml to about 50 ng/ml of purified Human Epidermal Growth Factor Receptor 2 (HER2) protein (R&D systems) was added to plates coated with anti-HER2 antibodies (R&D systems) and incubated. Then, calcein-AM was added and reaction mixture was again incubated. The result is shown in FIG. 4A (X axis: an amount of protein (ng/ml), Y axis: fluorescence intensity). As a comparative example, about 0.78 ng/ml to about 50 ng/ml of purified HER2 protein was added to plates coated with anti-HER2 antibodies and incubated. Then, quantification was performed using a general ELISA (anti-HER2 reaction) method. The result is shown in FIG. 4B (X axis: an amount of protein (ng/ml), Y axis: fluorescence intensity).

Figure 4B:
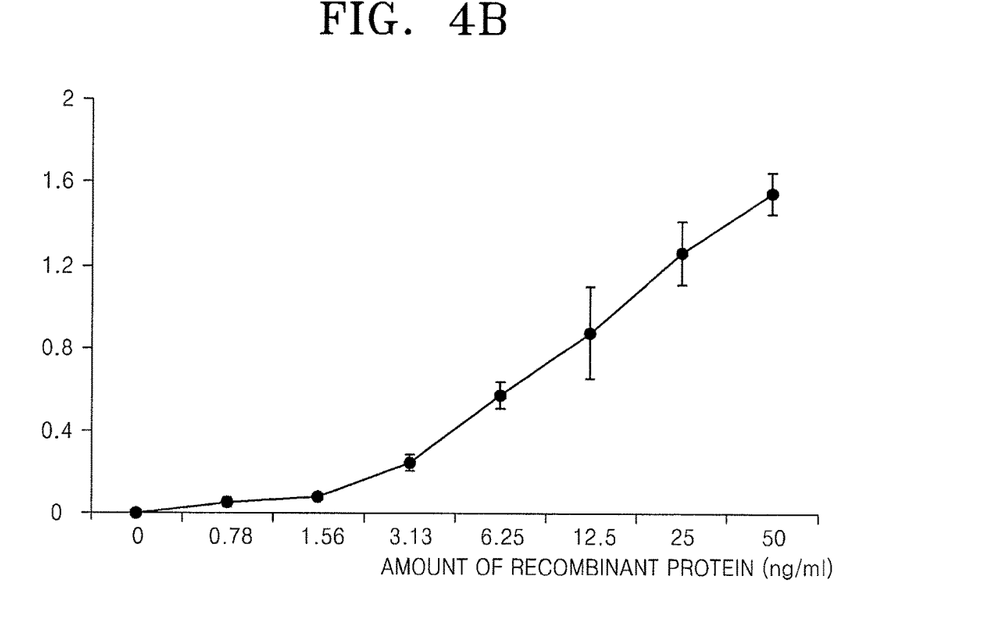

As shown in FIG. 4B, detection increased linearly with the quantity of the external proteins for the ELISA detection method even in the absence of microvesicles. On the other hand, as shown in FIG. 4A, the detection method using calcein-AM showed almost equal detection and quantification of microvesicles regardless of the quantity of HER2 protein contamination. Therefore, the calcein-AM detection method minimizes the effect of protein contamination on microvesicle detection and quantification.

Example 4. Screening of Antibodies with Binding Affinity for Microvesicles

To screen antibodies with high binding affinity for surface proteins of microvesicles, 5 anti-CD83 antibodies with different recognition sites for CD83 and EpCAM or 6 types of anti-EpCAM antibodies were coated to each well of a plate. 20 µl of plasma was added to each well and incubated, such that microvesicles containing CD83 or EpCAM surface proteins were captured. Afterwards, the microvesicles were stained by incubating the captured microvesicles with calcein-AM. Any calcein-AM that had not penetrated into microvesicles was washed off, and the fluorescence intensity was measured. The result of screening anti-CD83 antibodies is shown in FIG. 5A, and the result of screening anti-EpCAM antibodies is shown in FIG. 5B (X axis: tested capture antibodies, Y axis: fluorescence intensity).

Figure 5A:
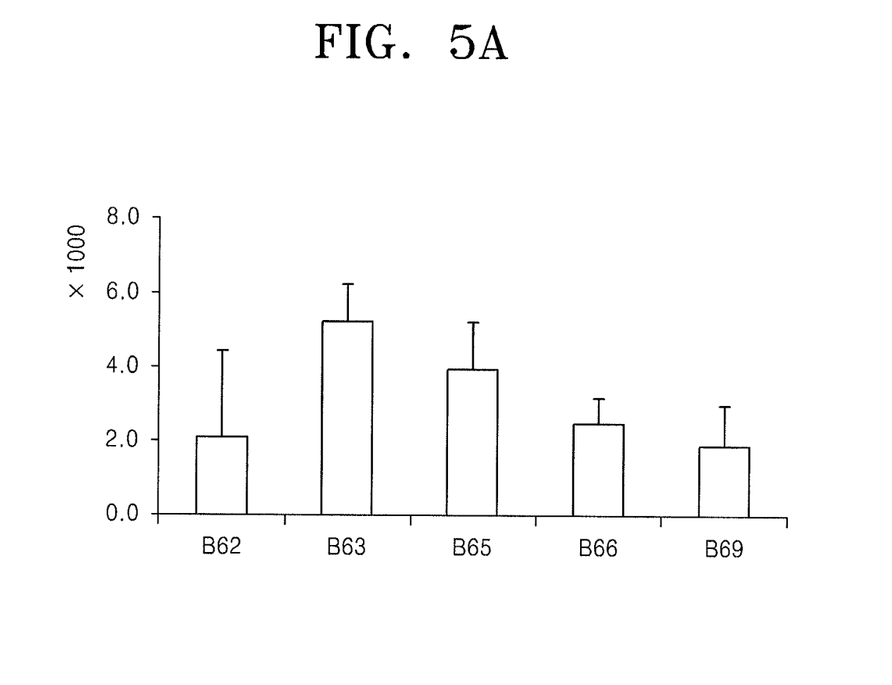
FIGS. 5A, 5B, 5C, and 5D are a graph, a graph, a gel image, and a gel image, respectively, that illustrate the results of screening antibodies with binding affinity for microvesicles. For FIGS. 5A and 5B, the Y axis represents fluorescence intensity.
Figure 5B:
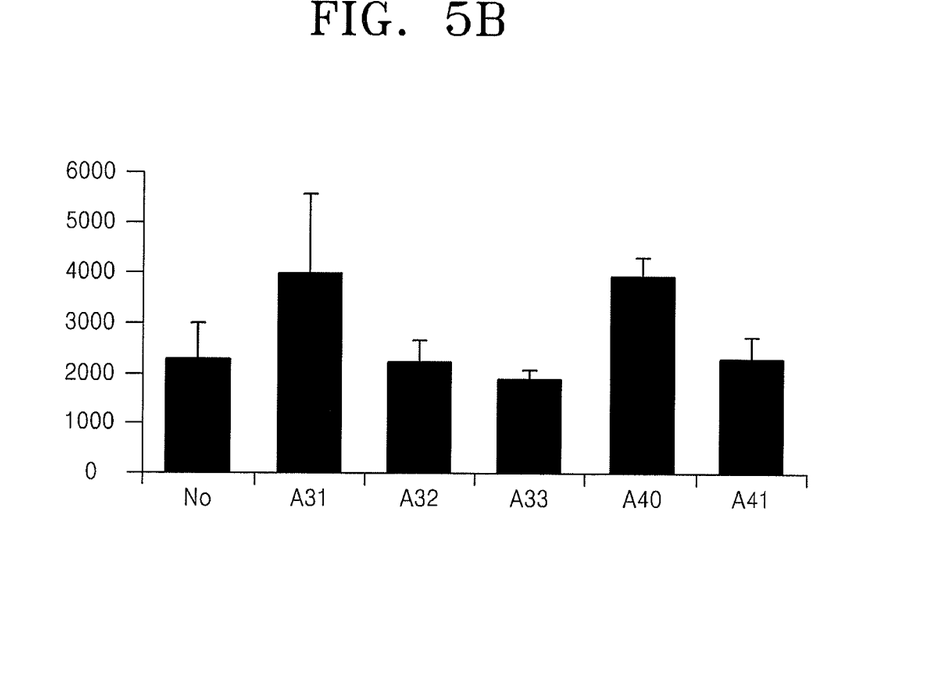

As shown in FIG. 5A, B63 antibody had high binding affinity for CD83. Also, as shown in FIG. 5B, A31 and A40 had binding affinities for EpCAM.

Figure 5C:
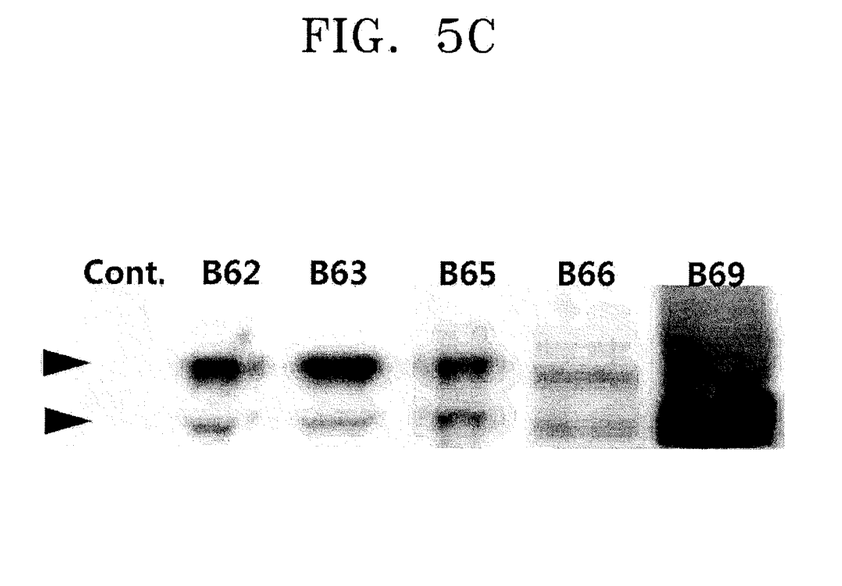
Figure 5D:
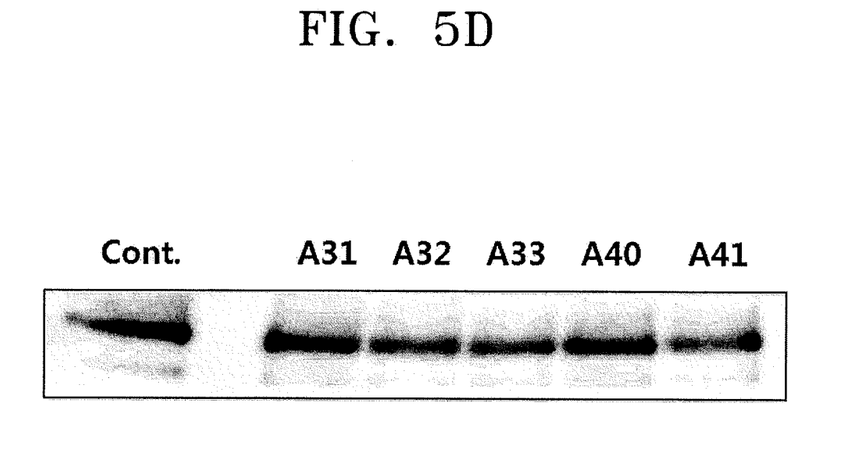

As a comparative example, antibodies were screened by an immunoprecipitation method using the anti-CD83 and anti-EpCAM antibodies to separate microvesicles from 300 µl of blood plasma. The microvesicles separated by immunoprecipitation were western blotted using microvesicle detecting antibodies. The result of screening anti-CD83 antibody was shown in FIG. 5C, and the result of screening anti-EpCAM antibody is shown in FIG. 5D.

As a result, similarly to the method using calcein-AM, B63 antibody had high binding affinity for CD83, and A31 and A40 antibodies had binding affinity for EpCAM.

As shown in FIGS. 5A to 5D, the results of screening for antibodies with high binding affinity for microvesicles were similar using either the calcein-AM detection method or western blotting method after immunoprecipitation. "Cont." in FIGS. 5C and 5D refers to a control group.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A method of analyzing a microvesicle in a sample, the method comprising:
   contacting a sample containing a microvesicle with a membrane permeable marker that is cleaved by an esterase and converted into a detectable marker inside the microvesicle;
   incubating the sample with an organic anion transport inhibitor before measuring the signal of the detectable marker; and
   measuring a signal of the detectable marker,
   wherein the microvesicle is an exosome, ectosome, or apoptotic bleb; and the membrane permeable marker is calcein-AM (calcein-acetoxymethyl ester), fura-2-AM (fura-2-acetoxymethyl ester), indo-1-AM (indo-1-acetoxymethyl ester), Indo-5F-AM (indo-5F-acetoxymethyl ester), quin-2-AM (ruin-2-acetoxymethyl ester), 5-CFDA-AM (5-carboxyfluorescein diacetate-acetoxymethyl ester), BAPTA-AM (bis(2-aminophenoxy)ethane tetraacetic acid-acetoxymethyl ester), 5,5'-difluoro BAPTA-AM, 5,5'-dimethyl BAPTA-AM, 5,5'-dinitro BAPTA-AM, BCECF-AM (2',7'-bis-(2-carboxyethyl)-5-(and-6)-carboxyfluorescein acetoxymethyl ester), dihydrocalcein-AM (dihydrocalcein-acetoxymethyl ester), EGTA-AM (EGTA-acetoxymethyl ester), fluo-3-AM (fluo-3-acetoxymethyl ester), fluo-8-AM (fluo-8-acetoxymethyl ester), rhod-2-AM (rhod-2-acetoxymethyl ester), rhod-4-AM (rhod-2-acetoxymethyl ester), rhod-5F-AM (rhod-5F-acetoxymethyl ester), rhod-5N-AM (rhod-5N-acetoxymethyl ester), X-rhod-1-AM (X-rhod-1-acetoxymethyl ester), or any combination thereof.

2. The method of claim 1, wherein the sample is a body fluid sample or a cell culture sample.

3. The method of claim 2, wherein the body fluid sample is urine, mucus, saliva, tears, blood plasma, blood serum, sputum, spinal fluid, hydrothorax, nipple aspirate, lymph, tracheolar fluid, intestinal fluid, genitourinary tract fluid, breast milk, lymph system fluid, semen, cerebrospinal fluid, tracheal system fluid, ascites, cystic tumor fluid, amniotic fluid, or any combination thereof.

4. The method of claim 1, further comprising incubating a ligand with the microvesicle to analyze a microvesicle protein, glycoprotein or lipid, wherein the ligand is a material having a binding affinity with a vesicle protein, glycoprotein, or lipid.

5. The method of claim 1, further comprising incubating at least two kinds of ligands with the microvesicle to screen the ligands for binding affinity, wherein the ligand is a material having a binding affinity with a vesicle protein, glycoprotein, or lipid.

6. The method of claim 1, wherein the organic anion transport inhibitor is sulfinpyrazone, probenecid, betamipron, cilastatin, 8-(noradamantan-3-yl)-1,3-dipropylxanthine, or any combination thereof.

7. The method of claim 1, further comprising incubating the sample containing the microvesicle with a ligand fixed on a solid support, wherein the ligand is a material having a binding affinity with a vesicle protein, glycoprotein, or lipid.

8. The method of claim 7, wherein the solid support is a polystyrene plate or a bead.

9. The method of claim 7, wherein incubating the sample containing the microvesicle with the ligand fixed on the solid support is performed before, after, or at the same time as contacting the sample with the membrane permeable marker that is converted into the detectable marker inside the microvesicle.

10. The method of claim 7, wherein the method further comprises washing a microvesicle that is bound to the ligand fixed on the solid support.

* * * * *